United States Patent [19]

Sheehan

[11] Patent Number: 4,605,005

[45] Date of Patent: Aug. 12, 1986

[54] WOUND CLOSURE DEVICE AND METHOD FOR USING SAME

[75] Inventor: Joseph C. M. Sheehan, Burr Ridge, Ill.

[73] Assignee: Kells Medical, Inc., Burr Ridge, Ill.

[21] Appl. No.: 661,375

[22] Filed: Oct. 16, 1984

Related U.S. Application Data

[63] Continuation-in-part of Ser. No. 472,053, Feb. 10, 1983, Pat. No. 4,526,173, which is a continuation-in-part of Ser. No. 367,671, Apr. 12, 1982, abandoned.

[51] Int. Cl.$^4$ .............................................. A61B 17/08
[52] U.S. Cl. ..................................... 128/335; 128/325; 128/326; 128/334 R; 128/337; 128/346
[58] Field of Search ................... 128/335, 334 R, 337, 128/325, 326, 346; 227/DIG. 1 B

[56] References Cited

U.S. PATENT DOCUMENTS

| | | | |
|---|---|---|---|
| 3,288,137 | 11/1966 | Lund | 128/DIG. 26 X |
| 4,141,363 | 2/1979 | James | 128/335 |
| 4,423,731 | 1/1984 | Roomi | 128/335 |
| 4,526,173 | 7/1985 | Sheehan | 128/335 |

OTHER PUBLICATIONS

Ad page "The Well Dressed Wound Wears Cover-Strip Wound Closure Strips" by Beiersdorf Inc. of Norwalk, CT.
3M Brochure SD-QAMB(102.5)II entitled "The Closure With Clout", from Surgical Products Division/3M, St. Paul, MN undated.
Dermizip-Skin Closure Manual, (Copyright 1982 by Kells Medical Inc.).

*Primary Examiner*—Lucille M. Phynes
*Attorney, Agent, or Firm*—Willian Brinks Olds Hofer Gilson & Lione Ltd.

[57] ABSTRACT

A wound closure device includes an elongated strip which defines first and second end sections and a central section. The central section includes a resilient element which defines a convex, generally cylindrical shape. In use, the entire strip, including both the end sections and the central section, is adhesively affixed to the skin with the resilient element flattened. Then the resilient element is allowed to return to its initial convex shape, thereby everting the skin in order to align both the epidermis and the germinal layer of the skin across the wound.

22 Claims, 7 Drawing Figures

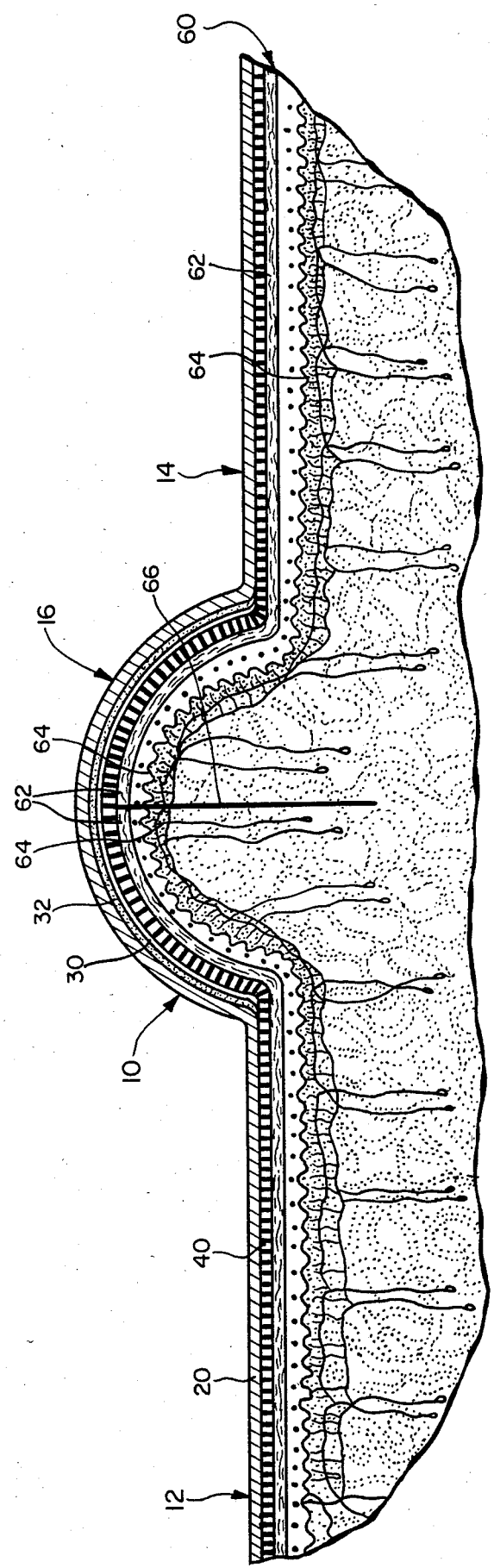

WOUND CLOSURE DEVICE AND METHOD FOR USING SAME

CROSS-REFERENCE TO RELATED APPLICATION

This application is a continuation-in-part of co-pending application Ser. No. 472,053, filed Mar. 10, 1983, now U.S. Pat. No. 4,526,173, which is in turn a continuation-in-part of application Ser. No. 367,671, filed Apr. 12, 1982, now abandoned.

BACKGROUND OF THE INVENTION

The present invention is directed to an improved adhesive strip-type wound closure device which operates to evert the skin adjacent to the wound in order to reduce the formation of scar tissue.

As discussed in detail in the above identified related applications, the skin is a complex structure which is made up of a number of distinct layers, including the epidermis or outer skin layer and the dermis, or germinal layer. It is the dermis or germinal layer which is the area of skin growth, and as pointed out in the above-identified related applications, remarkable reduction in scar tissue formation can be achieved by bringing both the epidermis and the germinal layer into proper alignment across the wound during wound closure. The full text of the related applications identified above is hereby incorporated by reference in this specification, and these related applications should be referenced for a more complete discussion of the nature of the various skin layers and the importance of bringing both the epidermis and the germinal layer into proper alignment in wound closure.

The related applications identified above disclose a number of wound closure devices which utilize both surfaces which are adhesively bonded to the epidermis and pins which are mechanically engaged to the dermis in order to achieve the desired alignment of both the epidermal and the germinal layers of the skin during wound closure. This approach has been found to provide remarkably efficient wound closure which minimizes the formation of scar tissue. However, in some applications, the full combination of adhesively bonded surfaces and mechanically engaging pins may not be required to achieve the desired alignment of the epidermis and dermis.

SUMMARY OF THE INVENTION

The present invention is directed to an improved adhesive strip wound closure device and method which enhance alignment of both the epidermis and the germinal layer by everting the skin adjacent to the wound.

According to one aspect of this invention, a wound closure device is provided for a wound in a region of skin which defines an epidermal layer and a germinal layer. This device comprises a strip which defines first and second end sections and a center section, as well as an adhesive layer which covers the first and second end sections and the center section and is adapted to secure each of the sections to the epidermal layer adhesively. The center section defines a selected convex shape and comprises a resilient material which operates to allow the center section to be flattened during application of the strip to the epidermal layer, and then to return to a convex shape after the adhesive layer has secured the sections to the epidermal layer, thereby everting the skin under the center section in order to enhance alignment of the germinal layer across the wound.

According to the method of this invention, the marginal edges of a wound are apposed and an adhesive strip is applied across the wound to the apposed epidermal layers. Then the skin is everted with the adhesive strip in a region which includes the wound, by an amount to appose the germinal layer across the wound in order to minimize scar tissue formation. The everting step can be accomplished either by allowing a resilient, preformed, curved center portion of the strip to return to its rest position, or by bending a rigid center section such that it takes on the desired curvature.

The present invention provides the important advantage that by everting the skin in the region of the wound, the tendency of the germinal layer to recoil from the wound is to a large extent counteracted. In this way, the alignment of the germinal layer and the epidermal layer across the wound is enhanced and wound healing is allowed to occur with a minimum of scar tissue formation. In the preferred embodiments described below, this important result is achieved without the use of pins or other elements which pierce the skin.

The invention itself, together with further objects and attendant advantages, will best be understood by reference to the following detailed description, taken in conjunction with the accompanying drawings.

BRIEF DESCRIPTION OF THE DRAWINGS

FIG. 4 is a sectional view taken along line 4—4 of FIG. 3b showing the embodiment of FIG. 1 as applied to close a skin wound.

DETAILED DESCRIPTION OF THE PRESENTLY PREFERRED EMBODIMENTS

Figure 1:
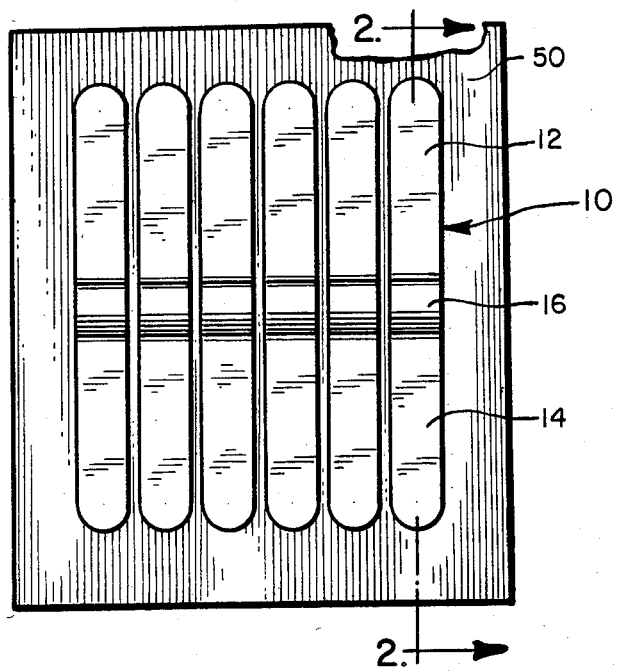
FIG. 1 is a perspective view showing a first preferred embodiment of the wound closure device of this invention.

Turning now to the drawings, FIG. 1 shows a perspective view of a first preferred embodiment of this invention. This embodiment includes a sheet of six separate adhesive strips 10. Each of the strips 10 comprises respective end sections 12,14 disposed on opposite sides of a respective central section 16.

Figure 2:
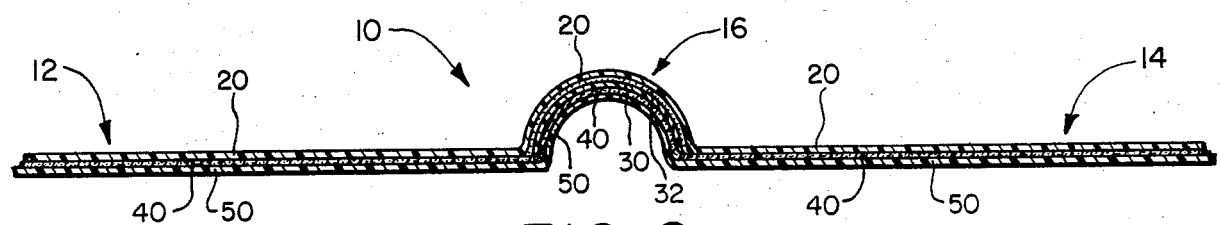
FIG. 2 is a sectional view taken along line 2—2 of FIG. 1.

FIG. 2 shows a cross-sectional view of one of the strips 10. As shown in FIG. 2, each of the strips 10 includes a flexible strip 20 which in this embodiment is a one-piece, flexible, plastic strip which extends over both the end sections 12,14 and the center section. A resilient, convexly-curved element 30 is adhesively bonded to the flexible strip 20 in the region of the central section 16 by a layer of adhesive 32. This resilient element 30 has a rest shape which defines a selected convex curvature, which in this preferred embodiment is substantially cylindrical with a radius of curvature of one quarter inch. As best seen in FIG. 2, the axis of symmetry of the cylindrical curvature of the resilient element 30 is oriented transversely to the length of the strip 10.

An adhesive layer 40 is secured to the exposed surfaces of the underside of both the flexible strip 20 and the resilient element 30. Thus, the adhesive layer 40 extends under both the end sections 12,14 and the central section 16. A backing strip 50 is secured to the exposed surface of the adhesive layer 40 in order to protect the adhesive layer 40 prior to use. The resilient element 30 is deformable such that it can be collapsed or flattened into a planar configuration during application, and will then return to a convex shape as shown in FIG. 4.

Figure 3A:
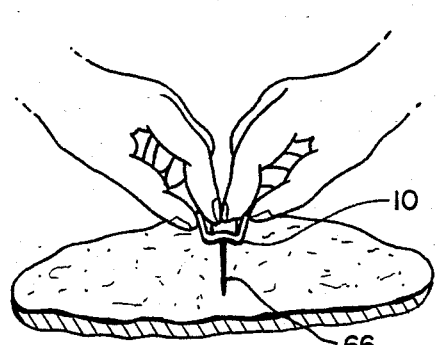
FIGS. 3a–3c are perspective views showing the method of use of the preferred embodiment of FIG. 1.
Figure 3B:
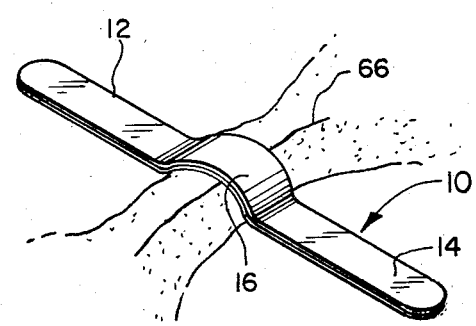
Figure 3C:
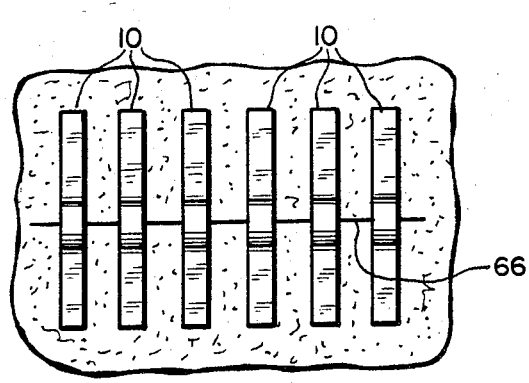

FIGS. 3a-3c are perspective views which illustrate various features of the use of the preferred embodiment of FIGS. 1 and 2. Prior to use, the skin surrounding the wound to be closed is cleaned and dried, and a suitable adhesive can, if desired, be applied over the entire region to be covered by the strip 10. Then, one of the strips 10 is removed from the backing sheet 50 and held with two hands, preferably as shown in FIG. 3a. Index digital pressure is then applied to the central section 16 in order to flatten the central section 16, and the strip then is positioned across the wound to be closed, with slight traction on the ends of the strip 10. The strip 10 is then pressed into position, after the epidermal layer has been brought properly into alignment. If necessary, forceps may be used in the conventional manner to appose the two sides of the wound properly prior to application of the strip 10. In this way, the central section 16 is securely adhesively bonded to the epidermal layer on both sides of the wound immediately adjacent to the marginal edges of the wound. Then the end sections 12,14 are pressed into adhesive engagement with the epidermal layer. Once the strip 10 has been adhesively bonded to the epidermal layer, it is then released. The resilient element 30 returns to the cylindrically convex shape shown in FIG. 4, thereby everting the edges of the skin at the central section 16 adjacent to the wound. FIG. 3b shows the maner in which a single strip 10 can be used to close a small wound and to evert the marginal edges of the skin adjacent to the wound, and FIG. 3c shows the manner in which an array of strips 10 can be used to close a longer wound in a similar manner. It should be noted that in each case the marginal edges of the skin adjacent to the wound are everted.

FIG. 4 is a cross-sectional view taken from FIG. 3b which illustrates the importance of everting the marginal edges of the skin. As shown in FIG. 4, the central section 16 is securely adhesively bonded to the epidermal layer 62 adjacent to the wound 66. For this reason, when the resilient element 30 returns to its convex shape, it everts the epidermal layer 62. This causes the underlying germinal layer 64 to be everted as well, thereby improving alignment of the germinal layer 64 across the wound 66 and counteracting the natural tendency of the germinal layer 64 to recoil from the wound 66. In this way, the formation of scar tissue is minimized.

It will be understood that a wide range of materials and manufacturing techniques can be used to form the strip 10. However, the following details are provided in order completely to define the presently preferred embodiment of this invention. It should be clearly understood that these details are provided only by way of illustration, and are not intended to be limiting in any way.

In this preferred embodiment, the flexible strip 20 is formed of a polyurethane material and is two and one-half inches in length and one-quarter inch in width. The polyurethane film distributed by J. P. Stevens & Co., Easthampton, Me., and identified as MP-1880 has been found to be suitable in a thickness of 0.005 inch. Such a polyurethane is sufficiently porous to allow the underlying skin to breathe and to minimize skin maceration. In this embodiment the resilient element 30 is formed of a 0.005 inch co-polyester film such as the material distributed by Eastman Chemical Products, Kingsport, Tenn., under the trade name Kodar. In this embodiment the resilient element 30 is adhesively bonded to the flexible strip 20 by a material such as the adhesive distributed by Fitchburg CPI as Type 594 medical adhesive. The adhesive layer 40 in this embodiment comprises a one-half mill layer of a polyester film which is coated with a double-sided adhesive; a suitable material is obtainable from Fitchburg CPI, coated with the above-identified Type 594 medical grade adhesive. One side of this adhesive secures the polyester strip to the exposed surfaces of the flexible strip 20 and the resilient element 30, and the other side of this adhesive secures the entire strip 10 to the epidermal layer of the skin. In this embodiment, the backing sheet 50 is formed of a film such as for example, the material distributed by H. P. Smith, Bedford Park, Ill., as 5 mill Natural H. D. Film - S #2071.

The presently preferred method for manufacturing the strip 10 begins with the lamination of each of the layers described above. Then a die-cut operation is performed to cut the flexible strip 20, the resilient element 30, and the adhesive layer 40 into strips of the desired width. A group of a number of strips 10 all adhesively secured to a single backing sheet 50 is then processed on a conventional heat sealing apparatus. This heat sealing apparatus is used to supply sufficient heat and pressure to form the resilient element 30 into the desired convex shape. The entire strip 10 is then cooled and packed in a suitable container. For example, the container can preferably be formed of the material marketed by DuPont under the trade name Tyvek. This material is permeable to ethylene oxide and the entire packaged assembly can then be sterilized with 100% ethylene oxide. In the heat sealing step, the heat and pressure should be chosen at values high enough to ensure the formation of the desired convex shape in the resilient element 30, yet not so high as to cause the materials in the adhesive layer 40 to flow or shrivel. In alternate embodiments, the heat sealing step can be performed directly during the lamination process.

Preferably, the strip 10 is sufficiently rigid in the central section 16 in order to evert the skin as shown in FIG. 4. Note that a straight line drawn between the points where the central section 16 joins the end sections 12,14 intersects the germinal layer 64. In this way, the desired forces are applied to the germinal layer 64 in order to obtain the desired apposition. In this embodiment, the rigidity of the resilient element 30 should be sufficient to evert the skin as shown in FIG. 4, yet not so rigid as to impede adhesive bonding between the central section 16 and the epidermal layer 62 during application of the strip 10 to the skin. In addition, an excessively rigid central section 16 can result in irritation to the epidermal layer 62 at the region where the central section 16 jois the end sections 12,14.

In an alternate embodiment, at least a center portion of an adhesive strip is made of a rigid material such as aluminum which can be bent to a desired shape after it has been applied to the epidermis across the wound. For example, a thin, flat aluminum strip can be provided with an adhesive layer on one side. Then, after the marginal edges of the wound have been apposed, the adhesive is used to securely bond the entire length of the strip to the skin as described above, with the strip bridging the wound. A forceps or other similar device is then used to bend or shape the strip into approximately the shape shown in FIG. 4 in connection with the first preferred embodiment. Because the aluminum strip is relatively rigid, it holds this curved shape, thereby everting the skin and apposing the germinal laayer across the wound as described above in connection with the first preferred embodiment.

This second embodiment is similar in terms of operation to the embodiment of FIGS. 1-4. However, the preformed, resilient element 30 has been eliminated and replaced by a rigid section which is bent to the desired skin everting shape after the strip has been secured to the skin.

Figure 5:
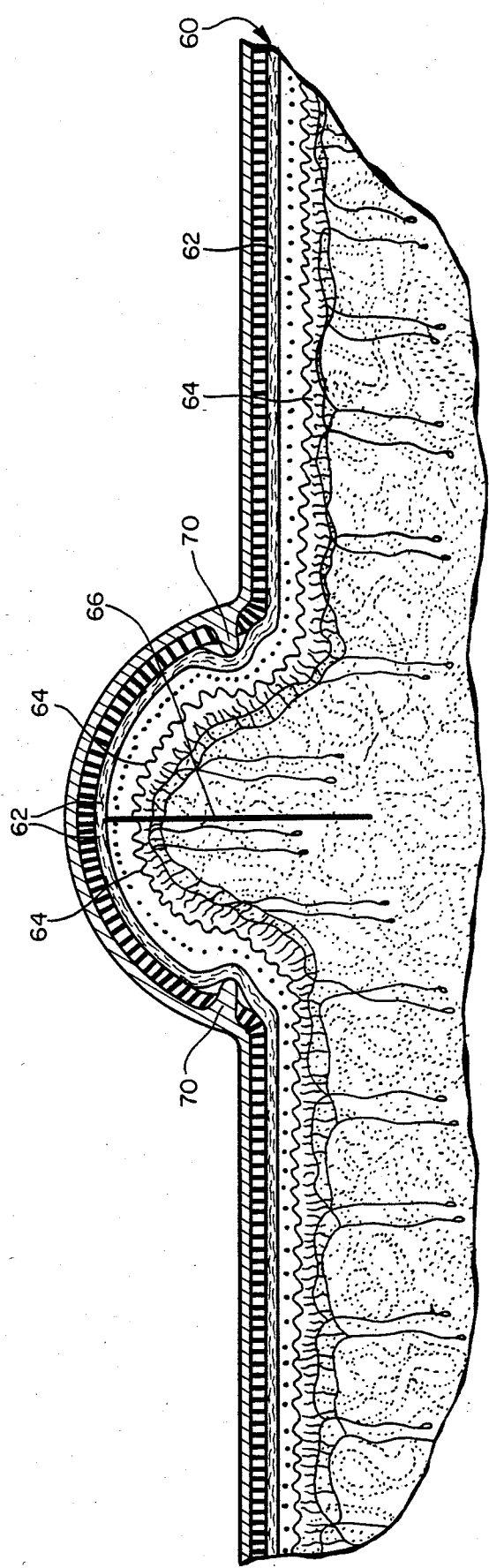
FIG. 5 is a cross-sectional view of a second preferred embodiment, taken in a plane similar to that of FIG. 4.

FIG. 5 shows another alternative embodiment which is in many ways similar to that of FIGS. 1-4. The principal difference is that the embodiment of FIG. 5 includes two molded protrusions 70 in the center section, each positioned to engage the skin mechanically without penetrating the skin. In this way slipping of the skin with respect to the strip is further impeded. In this embodiment the protrusions 70 are each about two millimeters in length. If desired, a pair of protrusions may be provided at each end of the center section to impede rotation of the skin under the strip.

From the foregoing, it should be apparent that an improved wound closure device has been disclosed. This wound closure device is an effective alternative to sutures or staples in many applications. It can be used to assist primary suture or staple closure or it can be used after suture or staple removal to support and protect the closure. The preferred embodiments described above evert the epidermal layer in order to provide excellent tissue apposition, excellent support and comfort, and substantially unconstricted blood flow to the closure. These embodiments manipulate the skin to sustain tissue eversion and apposition, which are important factors in proper healing. In addition, several of the preferred embodiments described above allow the skin to breathe and allow free wound drainage. It has been discovered that the embodiment described above in connection with FIGS. 1-4 generally results in a reddening of the skin under the strip 10 near the wound, and this reddening is believed to result from increased blood flow near the wound stimulated by the strip.

Of course, it should be understood that a wide range of changes and modifications can be made to the preferred embodiment described above. For example, other materials can be used for the flexible strip 20, such as woven materials including woven polyesters. Furthermore, other materials and dimensions can be changed as needed to fit individual applications. It may be desirable, for example, to form strips with center sections of varying dimensions, each matched to skin thickness of a selected body region. It is therefore intended that the foregoing detailed description be regarded as illustrative rather than limiting, and that it be understood that it is the following claims, including all equivalents, which are intended to define the scope of this invention.

I claim:

1. A wound closure device for a wound in a region of skin which defines an epidermal layer and a germinal layer, said device comprising:
    a strip defining first and second end sections and a center section;
    an adhesive layer covering the first and second end sections and the center section and adapted to adhesively secure each of the sections to the epidermal layer;
    said center section defining a selected convex shape and comprising a resilient material which operates to allow the center section to be flattened during application of the strip to the epidermal layer and then to return to a convex shape after the adhesive layer has secured the sections to the epidermal layer, thereby everting the skin under the center section in order to enhance alignment of the germinal layer across the wound.

2. The invention of claim 1 wherein the strip comprises:
    a flexible sheet which extends over the first and second end sections and the center section; and
    a resilient element secured to the flexible sheet in the center section of the strip, said resilient element shaped in said selected convex shape.

3. The invention of claim 1 wherein said selected convex shape comprises a generally cylindrical curvature which defines an axis of symmetry oriented substantially transversely to a line extending between the first and second end sections.

4. The invention of claim 2 wherein the flexible sheet comprises a polyurethane.

5. The invention of claim 1 wherein the strip defines an elongated shape.

6. The invention of claim 1 wherein the center section defines first and second ends adjacent the first and second end sections, respectively, wherein said selected convex shape defines a substantially cylindrical curvature, and wherein the generally cylindrical curvature is chosen such that, when the strip is adhesively secured to the skin, a straight line drawn between the first and second ends intersects the everted germinal layer under the center section.

7. The invention of claim 1 wherein the strip is approximately one-quarter inch in width.

8. The invention of claim 1 wherein the selected convex shape defines a substantially cylindrical curvature.

9. The invention of claim 1 wherein the center section defines a set of projections positioned to engage the epidermal layer mechanically to reduce relative movement between the epidermal layer and the center section.

10. A wound closure device for a wound in a region of skin which defines an epidermal layer and a germinal layer, said device comprising:
    a strip defining first and second end sections and a center section;
    an adhesive layer covering the first and second end sections and the center section and adapted to adhesively secure each of the sections to the epidermal layer;
    means, included in the center section of the strip, for resiliently everting the skin under the center section after the strip has been adhesively secured to the skin in order to enhance alignment of the germinal layer across the wound, said everting means being collapsible during application of the flexible strip to the skin to allow the center section to be securely adhesively bonded to the skin prior to eversion of the skin.

11. The invention of claim 10 wherein the everting means defines a rest shape having generally cylindrical curvature.

12. The invention of claim 11 wherein the generally cylindrical curvature defines first and second ends and wherein the generally cylindrical curvature is chosen such that, when the strip is adhesively affixed to the skin, a straight line drawn between the first and second ends intersects the everted germinal layer under the center section.

13. The invention of claim 11 wherein the generally cylindrically convex curvature defines an axis of symmetry oriented substantially tranversely to a line extending between the first and second end sections.

14. The invention of claim 10 wherein the center section defines a set of projections positioned to engage the epidermal layer mechanically to reduce relative movement between the epidermal layer and the center section.

15. A wound closure device for a wound in a region of skin which defines an epidermal layer and a germinal layer, said device comprising:
   a flexible, elongated strip which defines an underside;
   a resilient, semi-rigid element bonded to a central portion of the underside of the strip, said resilient element defining a generally cylindrical curvature; and
   a layer of adhesive secured to the resilient element and exposed portions of the underside of the strip to adhesively bond both the resilient element and the underside of the strip to the epidermal layer;
   said flexible strip, resilient element, and layer of adhesive cooperating to allow the resilient element to be flattened during application of the flexible strip to the epidermal layer and then to return to a convex curvature after the layer of adhesive has secured the strip and the resilient element to the epidermal layer, thereby everting the skin under the resilient element in order to enhance alignment of the germinal layer across the wound.

16. The invention of claim 15 wherein said generally cylindrical curvature defines an axis of symmetry oriented substantially tranversely to the elongated strip.

17. The invention of claim 15 wherein the flexible strip comprises a polyurethane.

18. The invention of claim 15 wherein the flexible strip is approximately one-quarter inch in width.

19. The invention of claim 15 wherein the resilient element defines first and second ends spaced along a convex curve defined by the generally cylindrical shape, and wherein the generally cylindrical shape is chosen such that, when the flexible strip and the resilient element are adhesively secured to the skin, a straight line drawn between the first and second ends intersects the everted germinal layer under the resilient element.

20. A method of closing a wound in a region of skin which defines an epidermal layer and a germinal layer, said method comprising the following steps:
   apposing the marginal edges of the wound;
   applying an adhesive strip across the wound to the apposed epidermal layers; and
   everting the skin with the adhesive strip in a region which includes the wound, by an amount sufficient to appose the germinal layer across the wound in order to minimize scar tissue formation.

21. The method of claim 20 wherein the adhesive strip comprises a preformed resilient center section which defines a selected curvature; wherein the applying step comprises the step of flattening the resilient center section against the epidermal layer across the wound; and wherein the everting step comprises the step of releasing the adhesive strip to allow the resilient center section to return to the selected curvature, thereby everting the skin.

22. The method of claim 20 wherein the adhesive strip comprises a rigid, bendable center section; and wherein the everting step comprises the step of bending the center section to impart a curvature to the center section after the center section has been adhesively secured to the epidermal layer, thereby everting the skin.

* * * * *